US005910301A

United States Patent [19]

Farr et al.

[11] Patent Number: 5,910,301

[45] **Date of Patent: *Jun. 8, 1999**

[54] METHOD OF INTRAPULMONARY ADMINISTRATION OF A NARCOTIC DRUG

[75] Inventors: Stephan J. Farr; Antony M. Rowe, both of Cardiff, United Kingdom; Reid Rubsamen, Hayward, Calif.

[73] Assignee: Aradigm Corporation, Hayward, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/813,094

[22] Filed: Mar. 7, 1997

Related U.S. Application Data

[63] Continuation of application No. 08/242,223, May 13, 1994, abandoned.

[51] Int. Cl.$^6$ .......... A61K 9/12

[52] U.S. Cl. .......... 424/45; 424/46

[58] Field of Search .......... 424/45, 46

[56] References Cited

U.S. PATENT DOCUMENTS

| | | |
|---|---|---|
| 3,812,854 | 5/1974 | Michaels et al. . |
| 4,814,161 | 3/1989 | Jinks et al. . |
| 5,225,183 | 7/1993 | Purewal et al. . |
| 5,230,884 | 7/1993 | Evans et al. . |
| 5,439,670 | 8/1995 | Purewal et al. . |
| 5,485,827 | 1/1996 | Zapol et al. . |
| 5,497,944 | 3/1996 | Weston et al. . |
| 5,589,156 | 12/1996 | Henry . |
| 5,653,961 | 8/1997 | McNally et al. . |
| 5,674,471 | 10/1997 | Akehurst et al. . |

FOREIGN PATENT DOCUMENTS

| | | |
|---|---|---|
| 3602370 | 8/1987 | Germany . |
| 2 255 918 | 11/1992 | United Kingdom . |
| 2 256 805 | 4/1994 | United Kingdom . |
| 90/07333 | 7/1990 | WIPO . |

OTHER PUBLICATIONS

Weinhold, L.L. et al., (1993) *Pharmacol. Biochem. Behav.* 44(1):141–144.

Jaffe, A.B. et al., (1989) *Psychopharmacology* 99(3):289–293.

Newman, S.P. et al., (1981) *Eur. J. Respir. Dis.* 62:3–21.

Newman, S.P., et al., "How should a pressurized β–adrenergic bronchodilator be inhaled?", *Eur. J. Respir. Dis.*, 62:3–21, (1981).

*Primary Examiner*—Raj Bawa

*Attorney, Agent, or Firm*—Karl Bozicevic; Bozicevic, Field & Francis LLP

[57] ABSTRACT

An aerosol formulation of an aerosol propellant and a base form of a narcotic drug selected from the group consisting of fentanyl, sufentanil and remfentanyl is provided. Such a formulation allows for the drug to be dissolved within the propellant and used within a device which does not require the use of a lubricant. Formulations are also disclosed which include lubricants, wherein the lubricant and propellant are both either polar or both non-polar. Thus, the lubricant component does not act as a solvent or cosolvent, but rather acts as a lubricant for the valve used for dispersing the formulation to a patient. Typical non-polar propellants include chlorofluorocarbons, which are typically used in connection with non-polar lubricants such as saturated vegetable oils, e.g. fractionated coconut oils. Typical polar propellants include hydrofluoroalkanes, which are typically used in connection with polar lubricants such as polyethylene glycols.

5 Claims, 1 Drawing Sheet

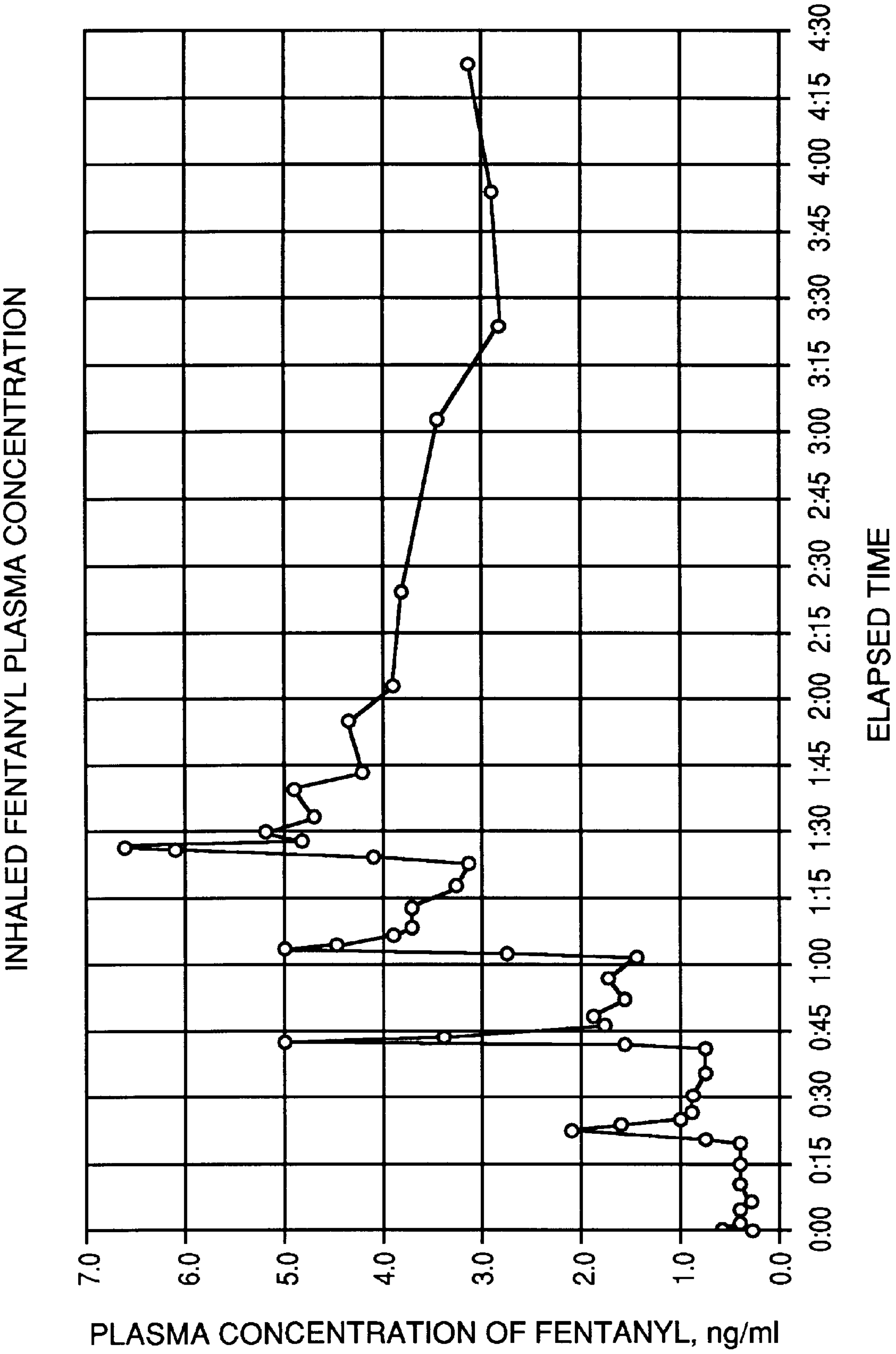
INHALED FENTANYL PLASMA CONCENTRATION
ELAPSED TIME
0:00 0:15 0:30 0:45 1:00 1:15 1:30 1:45 2:00 2:15 2:30 2:45 3:00 3:15 3:30 3:45 4:00 4:15 4:30
PLASMA CONCENTRATION OF FENTANYL, ng/ml
7.0 6.0 5.0 4.0 3.0 2.0 1.0 0.0

METHOD OF INTRAPULMONARY ADMINISTRATION OF A NARCOTIC DRUG

This is a continuation of application Ser. No. 08,242,223, filed May 13, 1994, now abandoned.

FIELD OF THE INVENTION

This invention relates generally to narcotic formulations useful in pain management. More specifically, this invention relates to formulation of a narcotic in a low boiling point propellant useful for the intrapulmonary delivery of narcotics to a human patient.

BACKGROUND OF THE INVENTION

Narcotic therapy forms the mainstay of pain management. Narcotics can be administered in many forms to patients with postsurgical and other forms of acute and chronic pain. Morphine, one of the oldest narcotics, is available for administration in tablet or in injectable form. Fentanyl, a synthetic narcotic, was first synthesized in 1960 by Paul Janssen and found to be 150 times more potent than morphine [Theodore Stanley, "The History and Development of the Fentanyl Series," *Journal of Pain and Symptom Management* (1992) 7:3 (suppl.), S3–S7]. Fentanyl and its relatives Sufentanil and Alfentanil are available for delivery by injection. In addition, fentanyl is available for administration by a transdermal delivery system in the form of a skin patch [Duragesic™ (fentanyl transdermal system) package insert, Janssen Pharmaceutica, Piscataway, N.J. 08855, January–June 1991].

A feature of the synthetic narcotic fentanyl is that it has a more rapid time to onset and a shorter duration of action than morphine. This makes fentanyl a useful drug for the management of acute pain. Currently, fentanyl is typically given by intravenous injection for acute pain management. Although fentanyl can be given by a transdermal patch, transdermal delivery of fentanyl is designed for long-term administration of the drug and does not lend itself to achieving a peak level rapidly for a short-term effect.

An alternative to delivery by injection for narcotics is delivery by inhalation. Morphine [J. Chrusbasik et al., "Absorption and Bioavailability of Nebulized Morphine," *Br. J. Anaesth.* (1988) 61, 228–30], fentanyl [M. H. Worsley et al., "Inhaled Fentanyl as a Method of Analgesia," *Anaesthesia* (1990) 45, 449–51], and sufentanil [A. B. Jaffe et al., "Rats Self-administer Sufentanil in Aerosol Form," *Psychopharmacology,* (1989) 99, 289–93] have been shown to be deliverable as aerosols into the lung. The pilot study described by Worsley suggested that "inhaled fentanyl is an effective, safe and convenient method of analgesia which merits further investigation."

Inhalation of a potent synthetic narcotic aerosol provides a mechanism for the non-invasive delivery of rapid-acting boluses of narcotic. The on-demand administration of boluses of narcotic coupled with a controlled baseline intravenous infusion of narcotic is termed "patient-controlled analgesia" (PCA) and has been found to be a very effective means of postoperative pain management.

Demand analgesia was first introduced in 1968 by Schetzer who showed it to be an effective mechanism for treating postoperative patients [Maureen Smythe, "Patient-Controlled Analgesia: A Review," *Pharmacotherapy* (1992), 12:2, 132–43]. Prior to the availability of patient-controlled analgesia, the paradigm for postoperative pain management consisted of intermittent intramuscular injections of narcotic. The cycle of the patient feeling pain, calling the nurse who then must locate and bring the drug to the bedside for administration results in suboptimal postoperative pain management [Philip Shade, "Patient-controlled Analgesia: Can Client Education Improve Outcomes?," *Journal of Advanced Nursing* (1992) 17, 408–13].

Postoperative pain management by intermittent narcotic administration has been shown to be a largely ineffective method of pain management for many of the patients undergoing the more than 21 million surgical procedures in the U.S. each year [John Camp, "Patient-Controlled Analgesia," *AFP* (1991), 2145–2150]. Even if every patient reliably received a constant dose of narcotic postoperatively, studies of therapeutic narcotic pharmacokinetic data have shown that patient variability makes such an approach fundamentally unsound and potentially dangerous [L. E. Mather, "Pharmacokinetics and Patient-Controlled Analgesia," *Acta Anaesthesiologica Belgica* (1992) 43:1, 5–20].

The first commercial device for automatically providing intravenous patient-controlled analgesia was developed in Wales in the mid-1970s. This device, the Cardiff Palliator (Graesby Medical Limited, United Kingdom) is the predecessor of numerous currently available computer-controlled patient-controlled analgesia intravenous pumps [Elizabeth Ryder, "All about Patient-Controlled Analgesia," *Journal of Intravenous Nursing* (1991) 14, 372–81]. Studies using these computer controlled intravenous narcotic infusion pumps have shown that small doses of narcotics given on demand by the patient provided superior pain relief when compared with intermittent intramuscular administration of these drugs [Morton Rosenburg, "Patient-Controlled Analgesia," *J. Oral Maxillofac Surg* (1992) 50, 386–89].

These computer-controlled pumps typically allowed for the programming of four different parameters: 1) basal intravenous narcotic infusion rate; 2) the bolus of narcotic to be delivered on each patient demand; 3) the maximum hourly total dose of narcotic to be allowed; and 4) the lockout period between doses. Typical programming for postoperative pain management with intravenous fentanyl might be a basal infusion rate of 20 μg/hr, a bolus demand dose of 20 μg, a maximum hourly dose of 180 μg, and a lockout period between doses of 5 minutes. In a study of 30 patients treated for postoperative pain with intravenous fentanyl patient-controlled analgesia, the minimum effective concentration (MEC) of fentanyl in the blood required to achieve pain relief in the group of patients studies was found to range from 0.23 to 1.18 ng/ml. Clinically significant respiratory depression was not seen in this study consistent with published data indicating that a fentanyl concentration of 2 ng/ml in the blood is typically required to depress the respiratory rate [Geoffrey Gourlay et al., "Fentanyl Blood Concentration—Analgesic Response Relationship in the treatment of Postoperative Pain," *Anesth Analg* (1988) 67, 329–37].

The administration of narcotic for pain management is potentially dangerous because overdoses of narcotics will cause complications such as respiratory depression. The patient's respiratory rate is decreased by the administration of narcotics. This decrease in respiratory rate may not be associated with a change in respiratory tidal volume [Miller, *Anesthesia* (*2nd ed*), *Churchill Livingston, I,* 762]. The four programmable parameters available on computer-controlled intravenous patient-controlled analgesia infusion pumps must be selected so as to minimize the likelihood of narcotic overdose. The preferred technique is to set the basal infusion rate at a relatively low rate and increase this rate based on how many times the patient presses the bolus demand button to self-administer supplemental drug.

As long as the patient himself or herself is the only one to push the demand button, respiratory depression is unlikely. However, there have been documented cases of the patient's family and friends pressing the narcotic demand button, for instance, while the patient is sleeping [Robert Rapp et al., "Patient-controlled Analgesia: A Review of the Effectiveness of Therapy and an Evaluation of Currently Available Devices," *DICP, The Annals of Pharmacotherapy* (1989) 23, 899–9040].

It is a problem with patient-controlled analgesia that it must currently be performed using an intravenous infusion pump. This requires that an indwelling catheter be placed in the patient's vein and that the patient transport a relatively bulky system with himself at all times to receive a baseline infusion of intravenous narcotic and allow for intermittent on-demand self-bolusing of additional narcotic in order to match the patient's changing need for drug. A portable PCA device incorporating a wristwatch-like interface has been described [D. J. Rowbotham, "A Disposable Device for Patient-Controlled Analgesia with Fentanyl," *Anaesthesia* (1989) 44, 922–24]. This system incorporated some of the features of computer-controlled programmable PCA infusion pumps such as basal infusion rate and the amount of each bolus. However, this system, which involved the use of an intravenous catheter as seen in larger infusion pumps, incorporated no provision to record accurately the actual dose of fentanyl administered to the patient over time.

Although fentanyl can be administered by transdermal patch, this method has been found to be suboptimal for postoperative main management [K. A. Lehmann et al., "Transdermal Fentanyl for the Treatment of Pain after Major Urological Operations, *Eur. J. Clin Pharmacol* (1991) 21:17–21]. Lehmann found that the low dose of narcotic delivered by transdermal fentanyl was inadequate to provide pain relief to many of his patients and that boosting the baseline infusion rate of the patch would put some patients at risk for having significant respiratory depression. In addition, he points out that if such a complication were to appear in conjunction with the delivery of narcotic by transdermal patch, the infusion could not be quickly stopped because the "cutaneous fentanyl depot" created by the transdermal patch would cause narcotic infusion to continue even after removal of the patch.

Delivery of fentanyl by aerosol used in conjunction with a non-invasively delivered long-acting preparation of narcotic such as slow-release oral morphine or a fentanyl transdermal patch provides a means for non-invasive administration of a basal rate of narcotic and rapid-acting boluses of narcotic to an ambulatory patient.

It is a problem with the aerosol delivery of fentanyl previously described that inefficient, bulky nebulizers must be used for the administration of the drug. In addition, these nebulizers work by administering from an open reservoir of the drug in aqueous solution allowing the vapor to be generally distributed and creating the potential for overdosing due to the lack of reproducible aerosol delivery. In addition, abuse through theft of the aqueous-phase fentanyl and subsequent unauthorized repackaging of this controlled substance in an aqueous injectable form are possible.

Because most surgery today is being done on ambulatory patients and because these patients are often rapidly discharged from the hospital and because patient-controlled analgesia has been identified as the preferred method of postoperative pain management, it is desirable to have a safe and effective method for non-invasive, ambulatory patient-controlled analgesia.

One attempt at providing a fentanyl containing aerosol formulation is disclosed within WO 90/0733 published Jul. 12, 1990 which teaches that in order to produce fentanyl containing aerosol compositions it is necessary to use a co-solvent and a surface active agent. The surface active agent is coated onto fentanyl and the co-solvent is combined with the propellant in order to create the formulation.

SUMMARY OF THE INVENTION

An aerosol formulation is disclosed which is comprised of (and may consist essentially only of) an aerosol propellant and a base form of a narcotic drug selected from the group consisting of fentanyl, sufentanil, and remifentanyl. Such a formulation allows for the drug to be dissolved within the propellant and used within a device which does not require the use of a lubricant. Formulations are also disclosed which include lubricants, wherein the lubricant and propellant are both either polar or both non-polar. Thus, the lubricant component does not act as a solvent or cosolvent, but rather acts as a lubricant for the valve used for dispersing the formulation to a patient. Typical non-polar propellants include chlorofluorocarbons, which are typically used in connection with non-polar lubricants such as saturated vegetable oils, e.g. fractionated coconut oils. Typical polar propellants include hydrofluoroalkanes, which are typically used in connection with polar lubricants such as polyethylene glycols.

A primary object of the invention is to provide an aerosol formulation consisting essentially of a propellant and a free base form of narcotic selected from the group consisting of fentanyl, sufentanil, and remifentanyl.

A feature of the invention is that the formulation does not include and does not require a co-solvent or surface active agent.

An advantage of the present invention is that only the minimum components necessary to propel the narcotic from the container and provide for the analgesic effect desired are present within the formulation.

Another advantage of the invention is that the formulation can be administered to obtain a particularly fast acting analgesic effect.

Another advantage is that the formulation can be used to provide an analgesic effect to ambulatory patients within seconds after being administered.

Another important object of the invention is to provide an aerosol formulation consisting essentially of a propellant, a free base form of a narcotic and a lubricant wherein the lubricant and propellant are both polar or both non-polar.

Another feature of the invention is that formulations containing no lubricant are dispersed from devices wherein the valve does not require a lubricant whereas formulations containing lubricant can be dispersed from any valve type.

Another advantage of the formulations of the invention is that the narcotic drug dissolves within the propellant without the need for a surfactant or co-solvent to form a formulation which does not include agglomeration of particles.

These and other objects, advantages and features of the present invention will become apparent to those skilled in the art upon reading this disclosure in combination with drawings wherein like numerals refer to like components throughout.

BRIEF DESCRIPTION OF THE DRAWING

FIG. 1 is a graph showing the results of an experiment plotting time vs. plasma level of fentanyl obtained with the invention.

DETAILED DESCRIPTION OF THE PREFERRED EMBODIMENTS

Before the present formulations used in pain management used in connection with the invention are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an antagonist" includes a plurality of such compounds, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The terms "analgesic drug" and "narcotic drug" are used interchangeably herein and shall be interpreted to mean a free base form of a drug selected from the groups consisting of fentanyl, sufentanil, and remifentanyl.

Terms such as "propellant", "aerosol propellant", "low boiling point propellant" and the like are used interchangeably herein to describe compounds generally used in connection with metered dose inhalers which compounds are liquified under pressure (many are gaseous at normal atmospheric pressure and temperature) and include chlorofluorocarbons, hydrofluorocarbons, hydrochlorofluorocarbons, hydrochlorocarbons, hydrocarbons, and hydrocarbon ethers.

The term "consisting essentially only of" is used herein to describe components of a formulation and shall mean that the formulation contains the specific components recited and contains less than 0.05% by weight of other components intentionally added and that the formulation may include minor acceptable levels of contaminant components in an amount of less than 0.05% by weight. The term excludes components intentionally added such as co-solvents and/or surface active agents which might be added to dissolve a drug and/or disperse drug particles (added for these normal functions). Formulations of the invention may consist essentially only of propellant, drug and a lubricant provided that the lubricant and propellant are both either polar or non-polar.

The terms "polar" and "non-polar" are used herein to describe the relative functional characteristics of one compound to another and specifically to define the solubility characteristics of the lubricant relative to the propellant. Polar lubricants are added to polar propellants and non-polar lubricants are added to non-polar propellants. Polar lubricants will dissolve readily in polar propellants and non-polar lubricants will dissolve readily in non-polar propellants. However, a polar lubricant will not have any or any significant effect on the solubility of the narcotic drug within the polar lubricant. Further, a non-polar lubricant will not have any or any significant effect on the solubility of a narcotic within a non-polar propellant. Thus, the lubricants are added only so as to provide lubrication to a valve and do not act as co-solvents or surfactants within the formulation and have no or no significant effect on the solubility of the narcotic within the propellant. The solubility characteristics of compounds such as lubricants and propellants are determined chiefly by their polarity. Non-polar or weekly polar lubricants dissolve in non-polar or weekly polar propellant solvents. Highly polar lubricants dissolve in highly polar propellant solvents—thus, like dissolves like. When a lubricant is added to a propellant both the lubricant and the propellant have the same or a sufficiently similar polarity (both are polar or both are non-polar) such that the lubricant does not act as a co-solvent, dispersing agent or surfactant. Accordingly, the lubricant will have no effect and/or a negligible effect on the solubility of the narcotic drug within the propellant. In accordance with a strict conventional definition of polar a molecule is polar if the center of negative charge does not coincide with the center of positive charge. Although our definition does not negate the strict conventional definition we expand such to indicate that a polar lubricant will dissolve within a polar propellant without any or any significant effect on the solubility of narcotic within the propellant e.g. the lubricant would have an effect of 20% or less on the solubility of narcotic drug within the propellant, preferably 10% or less and most preferably 0%.

FORMULATION IN GENERAL

Aerosol formulations disclosed are solutions, not suspensions, which consist essentially only of a low boiling point propellant and a free base form of a narcotic drug and a low boiling point propellant. The narcotic drug is a pharmaceutically pure free base form of a drug selected from the fentanyl, sufentanil, or remifentanyl.

Formulations consisting only of propellant and drug must be used in connection with devices which include valves which valves do not require a lubricant. Other formulations of the invention include a lubricant in relatively small amounts e.g. in the range of 0.01% to 0.5% by weight. When a lubricant is present the lubricant and the propellant are both polar or are both non-polar. Thus, the lubricant does not act as a co-solvent or surfactant within the formulation.

Specific low boiling point propellants have been found to be particularly useful in creating formulations of the invention. These propellants are as follows:

Formula I

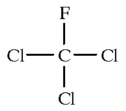

Formula II

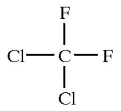

-continued

Formula III

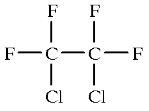

Formula IV

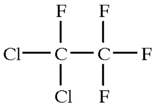

Formula V

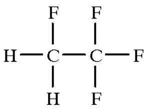

Formula VI

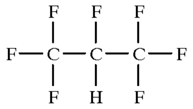

The narcotic drug component is added to the propellant component as a dry powder. The dry powder includes particles which dissolve in and form a solution with the propellant. The narcotic drug component may comprise as much as 5% of the formulation (solution) but is generally present in an amount of 0.5% by weight or less based on the volume of the total formulation, i.e. the combination of the propellant and narcotic drug. In general, the narcotic will be present in the formulation in an amount of about 0.5% to 0.01% by volume.

The narcotic drug is combined with the propellant and included within a pressurized aerosol inhaler container of the type generally used in connection with metered dose inhalers (MDIS). The container includes a valve which upon opening will release a metered dose of formulation. When released the propellant within the formulation will "flash" and become mostly gaseous, leaving a small amount of supercooled propellant and the particles of narcotic drug. The remainder of the propellant evaporates as it moves toward the lungs so that only particles will be delivered to the patient.

The formulation does not include co-solvents and/or surfactants in useful amounts, i.e. amounts such that the co-solvent could or does effect the ability of the drug to dissolve in the propellant solvent and/or cause particles to intermix therein in a uniform dispersion. The ability to create a formulation wherein the narcotic drug is uniformly dissolved within the propellant without using any co-solvent and/or surfactant is a particularly important aspect of the present invention. Accordingly, further explanation is provided below.

When a formulation of the invention includes only the propellant and no solvents or surfactants, the formulation is used in connection with a valve which does not require any lubricant. An example of such a valve is BK 357 available commercially from Bespak. The valve has been shown to provide for reproducible metering of doses of drug released from a conventional metered dose inhaler when using various conventional propellants, including chlorofluorocarbons, hyrofluorocarbons, 134a, and blends of hydrofluorocarbons with ethanol. Those skilled in the valve art will understand that formulations of the invention which include only the propellant and drug dissolved therein can be used in connection with other valves, provided those valves are designed to operate without the use of a lubricant. It is pointed out that, when the salt form of a drug such as fentanyl citrate is formulated with a propellant without the use of a co-solvent and/or surfactant, the resulting formulation creates a suspension composed of overtly agglomerated particles of drug which is essentially not usable in a conventional metered dose inhaler. However, by using the base form of the drug as per formulations described herein, it is possible to obtain formulations wherein the drug is dissolved in the propellant.

It is known that, in order for a surfactant component to act as a surfactant, a polar molecule will be used in combination with a non-polar solvent. For example, the polar molecules within conventional soap act as surfactants with respect to the non-polar molecules in oil. Based on this conventional thinking, a conventional formulation will use a polar surfactant and/or co-solvent when the propellant solvent is non-polar. Alternatively, when the propellant is polar, the surfactant and/or co-solvent is non-polar. Thus, conventional formulations use solvents and/or surfactants for their conventional effect of intermixing the propellant with the drug which eliminates the agglomeration of drug particles and provides for a more uniform formulation which can be dispersed from a conventional metered dose inhaler device.

Formulations of the present invention do not require the use of surfactants and/or co-solvents. However, if the formulation is to be used with a valve which requires lubrication, the lubricant should be included within the formulation. The lubricants included are not being included as co-solvents and/or surfactants. Specifically, when the formulation is one which includes a propellant which is non-polar, such as a chlorofluorocarbon, the lubricant used is also non-polar. Thus, the non-polar lubricant does not act as a conventional surfactant and/or co-solvent. Examples of such non-polar lubricants to be used with non-polar propellants are saturated vegetable oils, for example, a series of fractionated coconut oils available commercially as Miglyol 812, 829 and 840. Other vegetable oils and/or non-polar molecules conventionally used as lubricants could also be included within the formulation when non-polar propellants are used to formulate.

When a formulation of the invention is prepared using a polar propellant such as a hydrofluoroalkane (HFA) and the formulation is used in a device having a valve which requires a lubricant, the formulation will include a polar lubricant such as polyethylene glycol, examples of which are available as PEG 100, 200, 300, 400, 600, 1000, and 1500. Other polar molecules with lubricating properties could also be used in connection with formulations of the invention wherein the propellant is comprised of polar molecules.

Based on the above, it can be seen that formulations of the invention may include no co-solvents and/or surfactants and be used in connection with valves which do not require lubricants. However, the formulations may include compounds which might at first appear to have other functions, but which are actually acting only as valve lubricants. The lubricants provided within the formulations are polar when the propellant solvent is polar, and the lubricants are non-polar when the propellant solvent is non-polar. Thus, the lubricants do not provide for a co-solvent and/or surfactant effect within the formulation, and are present only in amounts sufficient to provide for valve lubrication when they are used in connection with valves which require a lubricant. The lubricant and propellant are sufficiently similar regarding their polarity that the lubricant has no or substantially no effect as a co-solvent and/or dispersant i.e. does not effect the solubility and/or dispersability of the drug in the propellant.

The drug particles consist essentially only of the narcotic drug i.e. the free base form (and not the salt form) of a drug selected from the group consisting of fentanyl, sufentanil, and remifentanyl. Narcotic drugs such as these are normally present and formulated in their salt form. For example, fentanyl is normally present as fentanyl citrate which is shown below:

Formula VII

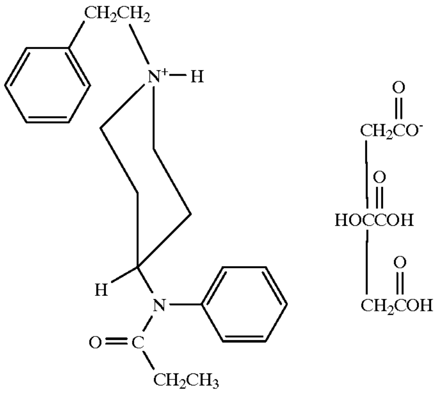

Fentanyl Citrate

In accordance with processing disclosed herein the citrate form or other salt form of fentanyl may be used to obtain the free base form of the drug used in formulations of the present invention. The free base form of fentanyl is shown below:

Formula VIII

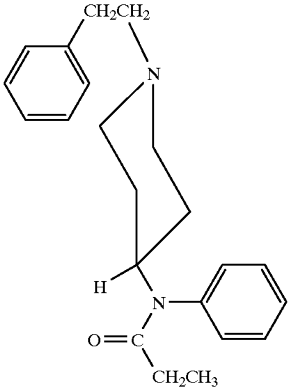

Fentanyl Free Base

With respect to each of the narcotic drugs the salt form is generally used as a starting material. The salt form is then processed in order to obtain the free base of the drug. The free base form of the drug is dissolved in a propellant to provide a drug/propellant solution which is the formulation of the present invention. If the free base form of the drug is not created then it will not be possible to dissolve the drug in the propellant and create the formulation without the use of co-solvents and/or surfactants in relatively high amounts.

The structural formula of the free base form of other preferred narcotic drugs used in connection with the present invention are shown below. Preferred narcotic drugs include the free base form of fentanyl, sufentanil, and remifentanil with remifentanil being particularly preferred due to its fast-acting narcotic effect.

Formula IX

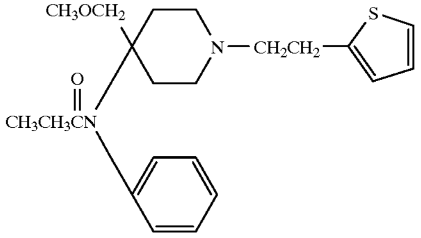

Sufentanil Free Base

Formula X

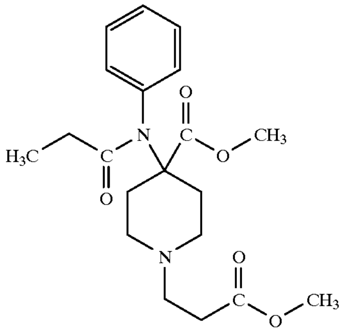

Remifentanil Free Base

PREPARATION OF NARCOTIC FREE BASE

The free base form of various narcotic drugs are shown above. This free base form of the drug is, in general, created by using the salt form, such as fentanyl citrate, as the starting material. The salt form of the drug is dissolved in water and then combined with a strong base such as ammonia which, in water, forms ammonium hydroxide. It is possible to precipitate out the free base form of the drug from such a solution. Thereafter, various purification processing is carried out in order to obtain pharmaceutically pure drug in the free base form. It is the pure form of the free base drug which is combined with a propellant in order to form formulations of the present invention.

PROPELLANTS

Propellants used in connection with the interpulmonary delivery of drugs are described by using two or three digits. When two digits are present the first digit is assumed to be zero. The first digit is one less than the number of carbon atoms in the compound. Accordingly, if the first digit is one in a three digit number the compound includes two carbon atoms. If the propellant is designated by only two digits the first digit is assumed to be zero and the compound includes only a single carbon atom. The second digit describing the propellant is one more than the number of hydrogen atoms in the compound. Accordingly, if the second digit is one the compound includes no hydrogen atoms. The third and last digit represents the number of fluorine atoms in the compound.

The above information can be used to determine the chemical composition of any propellant described by three digits when the propellant is comprised of carbon, hydrogen and fluorine atoms. However, some propellants also include chlorine atoms. The number of chlorine atoms in the compound is found by subtracting the sum of the fluorine and hydrogen atoms from the total number of atoms which can be added to saturate the carbon chain. Thus, a propellant described as 114 indicates that the propellant includes two carbon atoms. The second 1 in the number indicates that the compound includes 0 hydrogen atoms. The third digit "4" indicates that the compound includes four fluorine atoms. Since two carbon atoms would be saturated with the presence of six attached atoms the propellant must include two chlorine atoms.

Some propellants are isomers of each other. When isomers exist the propellant compound which is the most symmetric compound is indicated by a number by itself. The isomer closest to that structure is indicated by the letter "a" following the number. As the degree of asymmetry increases the letters "b", "c" etc. are added. For cyclic compounds a "C" is used in front of the number. In order to show an example of two propellants which are isomers of each other the following structural formulas are provided for propellants 114 and 114a:

Formula III

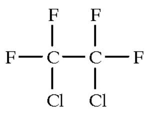

114

Formula IV

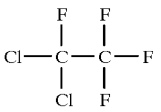

114a

SPECIFIC FORMULATIONS

Specific formulations of the invention are created by first creating the free base form of the drug as described generally above and as described specifically in Example 1. The free base form of the drug, in a dry powder state is dissolved in a propellant. Thereafter, for some formulations, a valve lubricant (non-polar or polar) is added. Examples of some useful formulation are as follows wherein all percentages are by weight.

| Formulation #1 | |
|---|---|
| fentanyl free base | 1.0% |
| propellant 227 | 99.0% |

-continued

| Formulation #2 | |
|---|---|
| sufentanil free base | 0.2% |
| propellant 134a | 99.8% |
| **Formulation #3** | |
| fentanyl free base | 0.1% |
| propellant 11 & 12 in 28:72 blend | 99.9% |
| **Formulation #4** | |
| remifentanyl free base | 0.01% |
| propellant 227 | 99.99% |
| **Formulation #5** | |
| fentanyl free base | 0.02% |
| propellant 227 & 134a in 50:50 blend | 99.98% |
| **Formulation #6** | |
| fentanyl free base | 0.95% |
| propellant (polar) | 99.0% |
| lubricant (polar) | 0.05% |
| **Formulation #7** | |
| sufentanil free base | 0.15% |
| propellant (non-polar) | 99.8% |
| lubricant (non-polar) | 0.05% |
| **Formulation #8** | |
| fentanyl free base | 0.1% |
| propellant (polar) | 99.85% |
| PEG 300 | 0.05% |
| **Formulation #9** | |
| remifentanyl free base | 0.01% |
| propellant (non-polar) | 99.94% |
| oil | 0.05% |
| **Formulation #10** | |
| sufentanil free base | 0.02% |
| propellant (HFA polar) | 99.93% |
| PEG 300 | 0.05% |
| **Formulation #11** | |
| fentanyl free base | 1.0% |
| propellant CFC | 98.95% |
| Miglyol 812 | 0.05% |
| **Formulation #12** | |
| sufentanil free base | 0.2% |
| propellant (HFA) | 99.75% |
| PEG 100 | 0.05% |
| **Formulation #13** | |
| fentanyl free base | 0.1% |
| propellant (blend of polar and non-polar) | 99.9% |
| **Formulation #14** | |
| remifentanyl free base | 0.01% |
| propellant 114 | 99.94% |
| Miglyol 829 | 0.05% |
| **Formulation #15** | |
| remifentanyl free base | 0.02% |
| propellant 227 & 134a in 50:50 blend | 99.98% |
| **Formulation #16** | |
| fentanyl free base | 0.95% |
| propellant (HFA) | 99.0% |
| PEG 300 | 0.05% |
| **Formulation #17** | |
| sufentanil free base | 0.15% |
| propellant 134a | 99.8% |
| Miglyol 840 | 0.05% |

-continued

Formulation #18

| | |
|---|---|
| fentanyl free base | 0.1% |
| propellant 11 & 12 in 28:72 blend | 99.85% |
| fractionated coconut oil | 0.05% |

Formulation #19

| | |
|---|---|
| remifentanyl free base | 0.01% |
| propellant 227 | 99.94% |
| saturated oil | 0.05% |

Formulation #20

| | |
|---|---|
| free base | 0.02% |
| propellant 227 & 134a in 50:50 blend | 99.93% |
| lubricant | 0.05% |

Comparative Formulations

Comparative #21 (no surfactant/cosolvent)

| | |
|---|---|
| fentanyl citrate | 15.71 mg |
| Span 85 | 0 |
| p11 | 1.913 g |
| p12 | 4.920 g |
| total (5 ml) | 6.849 g |

Comparative #22 (0.05% surfactant)

| | |
|---|---|
| fentanyl citrate | 15.71 mg |
| Span 85 | 3.42 mg |
| p11 | 1.912 g |
| p12 | 4.918 g |
| total (5 ml) | 6.849 g |

Comparative #23 (0.5% surfactant)

| | |
|---|---|
| fentanyl citrate | 15.71 mg |
| Span 85 | 34.2 mg |
| p11 | 1.904 g |
| p12 | 4.845 g |
| total (5 ml) | 6.849 g |

Unlike formulations of the present invention which included no surfactant and/or co-solvent, comparative formulation #21 (with no surfactant/co-solvent) included overtly agglomerated particles.

Comparative Examples 22 and 23 are suspensions and not solutions. Examples 1–20 are solutions.

GENERAL METHODOLOGY

A non-invasive means of pain management is provided in a manner which makes it possible to maintain tight control over the amount of drug administered to a patient suffering with pain. The formulation is administered by intrapulmonary delivery in a controlled and repeatable manner. The formulation is preferably delivered from a device which is not directly actuated by the patient in the sense that no button is pushed nor valve released by the patient applying physical pressure. On the contrary, the device provides that the valve releasing analgesic drug is opened automatically upon receipt of a signal from a microprocessor programmed to send a signal when data is received from a monitoring device such as an airflow rate monitoring device. A patient using the device withdraws air from a mouthpiece and the inspiratory rate, and calculated inspiratory volume of the patient is measured one or more times in a monitoring event which determines an optimal point in an inhalation cycle for the release of a dose of analgesic drug. Inspiratory flow is measured and recorded in one or more monitoring events for a given patient in order to develop an inspiratory flow profile for the patient. The recorded information is analyzed by a microprocessor in order to deduce a preferred point within the patient's inspiratory cycle for the release of analgesic drug with the preferred point being calculated based on the most likely point to result in a reproducible delivery event.

The device preferably includes a flow rate monitoring device which continually sends information to the microprocessor, and when the microprocessor determines that the optimal point in the respiratory cycle is reached, the microprocessor actuates the opening of the valve allowing release of analgesic drug. Accordingly, drug is always delivered at a pre-programmed place in the inspiratory flow profile of the particular patient which is selected specifically to maximize reproducibility of drug delivery and peripheral deposition of the drug. It is pointed out that the device can be used to, and actually does, improve the efficiency of drug delivery. However, this is not the critical feature. The critical feature is the reproducibility of the release of a tightly controlled amount of drug at a particular point in the respiratory cycle so as to assure the delivery of a controlled and repeatable amount of drug to the lungs of each individual patient.

The combination of automatic control of the valve release, combined with frequent monitoring events in order to calculate the optimal flow rate and time for the release of analgesic drug, combine to provide a repeatable means of delivering analgesic drug to a patient. Because the valve is released automatically and not manually, it can be predictably and repeatedly opened for the same amount of time each time or for the preprogrammed measured amount of time which is desired at that particular dosing event. Because dosing events are preferably preceded by monitoring events, the amount of analgesic drug released and/or the point in the inspiratory cycle of the release can be readjusted based on the particular condition of the patient. For example, if the patient is suffering from a condition which allows for a certain degree of pulmonary insufficiency, such will be taken into account in the monitoring event by the microprocessor which will readjust the amount and/or point of release of the analgesic drug in a manner calculated to provide for the administration of the same amount of analgesic drug to the patient at each dosing event.

It has been found that the ability to tightly control the amount of a volatile propellant formulation of drug delivered via the intrapulmonary route can be improved by delivering smaller doses of the propellant/drug formulation with each release of the valve and with each dosing event. Repeatability, in terms of the amount of analgesic drug delivered to a patient, is improved when the analgesic drug is delivered during a smooth, normal inhalation by the patient. To a certain extent, the ability to provide for a smooth inhalation is enhanced when smaller amounts of analgesic drug are released as compared with larger amounts of analgesic drug. Accordingly, an important aspect of the invention is to deliver aerosolized analgesic drug to a patient in a series of interrupted bursts while the patient continues a single inhaled breath, with each burst being delivered while the patient maintains optimal inspiratory flow.

The amount of analgesic drug delivered to the patient will vary greatly depending on the particular drug being delivered. In accordance with the present invention it is possible to deliver different narcotic drugs. When sufentanil is administered it is generally administered to a patient in an amount in the range of about 10 $\mu$g to 100 $\mu$g. It is pointed out that sufentanil is approximately ten times more potent than fentanyl so that fentanyl is generally delivered to a patient in an amount of about 100 $\mu$g to 1000 $\mu$g. These doses are based on the assumption that when interpulmonary delivery methodology is used the efficiency of the delivery is approximately 10% and adjustments in the amount released must be made in order to take into account the efficiency of the device. The differential between the amount of analgesic drug actually released from the device and the amount of analgesic drug actually delivered to the patient varies due to a number of factors. In general, the device discussed above is approximately 20% efficient, however, the efficiency can be as low as 10% and as high as 50% meaning that as little as 10% of the released analgesic drug may actually reach the circulatory system of the patient and as much as 50% might be delivered. The efficiency of the delivery will vary somewhat from patient to patient and must be taken into account when programming the device for the release of analgesic drug. In general, a conventional metered dose inhaling device is about 10% efficient.

When administering analgesic drugs the entire dosing event can involve the administration of anywhere from 1 μg to 100 mg, but more preferably involves the administration of approximately 10 μg to 10 mg. The large variation in the amounts which might be delivered are due to the fact that different drugs have greatly different potencies and may be delivered from devices which vary greatly in terms of the efficiency of drug delivered. The entire dosing event may involve several inhalations by the patient with each of the inhalations being provided with one or more bursts of analgesic drug from the device.

In addition to drug potency and delivery efficiency, analgesic drug sensitivity must be taken into consideration. The present invention makes it possible to vary dosing over time if analgesic sensitivity changes and/or if user compliance and/or lung efficiency changes over time.

Based on the above, it will be understood that the dosing or amount of analgesic drug actually released from the device can be changed based on the most immediately prior monitoring event wherein the inspiratory flow of a patient's inhalation is measured.

EXAMPLES

The following examples are put forth so as to provide those of ordinary skill in the art with a complete disclosure and description of how to make the formulations and use the methodology of the invention and are not intended to limit the scope of what the inventor regards as his invention. Efforts have been made to ensure accuracy with respect to numbers used (e.g. amounts, temperature, etc.) but some experimental errors and deviation should be accounted for. Unless indicated otherwise, parts or parts by weight, molecular weight is weight average molecular weight, temperature is in degrees Centigrade and pressure is at or near atmospheric.

EXAMPLE 1

Obtaining Fentanyl Free Base

The free base form of fentanyl can be obtained by using fentanyl citrate (purchased from Sigma Chemicals). First, dissolve 500 mg of fentanyl citrate in 100 ml of distilled water. Mixing should be thorough, and is preferably carried out using sonification for approximately 60 seconds. Thereafter, adjust the pH of the solution to pH 10.0 by the dropwise addition of 2.5% v/v ammonium hydroxide solution. The free base form of fentanyl will precipitate out of solution as the pH is raised to approximately 10.0.

Transfer the solution to a 250 ml separating funnel. In order to ensure that all of the contents of the original beaker is transferred, wash the beaker with 25 ml of water and add the washings to the funnel. Wash the pH electrode, temperature probe and beaker with 25 ml of diethyl ether and add such to the separating funnel.

Add 100 ml of diethyl ether to the separating funnel. Thereafter, put a stopper in place and shake the contents. Thereafter, allow the contents to separate into two phases. Drain off and retain the lower aqueous phase. Transfer the organic layer to a weighed crucible cooled by resting on a bed of ice maintained at a temperature of approximately −15° C. by a cooling plate. Return the aqueous layer to the separating funnel and add an additional 50 ml of diethyl ether. Include the stopper and shake again. Drain off and discard the aqueous layer. Transfer the organic layer to a crucible and allow the ether to evaporate.

If needed, the crucible can be placed in a vacuum oven at approximately 45–50° C. overnight in order to thoroughly dry the residue. In order to confirm purity and yield, re-weigh the crucible to determine the residue weight. Carefully remove the residue from the crucible and weigh. Express this value as a percentage of the theoretical yield.

EXAMPLE 2

Determine Purity

Obtain the fentanyl free base in a dried, pure form in accordance with the procedures described in Example 1. Determine the purity by making a sample of known weight in methanol and running against a standard curve. The standard curve is determined by making a dilution series from a fentanyl citrate/methanol solution which gives known concentrations of fentanyl base.

EXAMPLE 3

Formulation Administration

Formulation consisting essentially only of fentanyl free base and propellant was delivered to a human patient. The patient was administered 50 μl of formulation, which amount of formulation contained 100 μg of fentanyl base. Accordingly, a patient was allowed to inhale a dose of 50 μl of formulation from a device as shown within FIG. 2 and described above.

The initial administration was of 100 μg of fentanyl resulting in the release of 50 μl of formulation. At intervals of 20 minutes, 40 minutes, 60 minutes and 80 minutes the patient was administered 200, 300, 400 and again 400 μg of fentanyl base respectively. Accordingly, the total cumulative amounts of fentanyl base administered to the patient was 100, 300, 600, 1,000 and 1,400 μg of fentanyl base. The plasma levels of fentanyl base found in the patient were determined in nanograms of fentanyl per milliliter of plasma.

The results shown in FIG. 1 indicate that the fentanyl appears in the patients blood within seconds after the administration by the interpulmonary route in accordance with the methodology and using the formulation of the present invention. The results are surprising in that particularly large percentage amounts of fentanyl are delivered to the patient based on the amount of fentanyl actually administered to the patient by the interpulmonary route. Further, the results are surprising in view of the relatively short time period from administration to the time period when the fentanyl actually appears in the patients blood.

In a previously published study of 30 patients treated for post-operative pain with intravenous fentanyl patient-controlled analgesia, the minimum effective concentration (MEC) of fentanyl in the blood required to achieve pain relief in the group of patients studied was found to range from 0.23 to 1.18 ng/ml. (See Gourlay et al. cited above). Accordingly, the formulation and methodology of the present invention can be used to quickly and efficiently achieve pain relief.

By using the formulations and methodology of the present invention it is possible to obtain a blood level of narcotic in the patient which is sufficient to provide for pain relief in a period of time of five seconds or less. Specifically, it is possible to obtain a blood level of narcotic such as fentanyl in the patient by administering a dose of formulation containing 100 μg of fentanyl base and thereby obtain a blood level above 1.5 ng/ml which is above the amount shown to provide for pain relief. Additional doses can be administered in order to provide for a higher degree of pain relief. This is clearly shown within FIG. 1. For example, by administering 300 μg of fentanyl base it is possible to obtain a blood level above 4.0 ng/ml. By administering 1,400 μg of fentanyl base it is possible to obtain a blood level above 6.0 ng/ml which amount is sufficient to provide for pain relief from even severe pain. Thus, the invention can be used to administer 50 μg to about 2,000 μg of narcotic to a patient by inhalation and obtain a blood level in the range of 1.5 to 6.5 ng/ml in a period of time of less than 1 minute. Thus the formulations and methodology of the invention provide for a means to obtain high levels of a narcotic in the blood plasma of a patient in a very short period of time.

The instant invention is shown and described herein in what is considered to be the most practical and preferred embodiments. It is recognized, however, that the departures may be made therefrom which are within the scope of the invention and that obvious modifications will occur to one skilled in the art upon reading this disclosure.

We claim:

1. A method of intrapulmonary administration of a narcotic drug, comprising:

determining a patient's inspiratory flow rate and inspiratory volume;

calculating a point in the patient's inspiratory cycle for release of an aerosol of narcotic drug wherein the point in that most likely to result in reproducible delivery;

releasing, at the calculated point, a metered dose of aerosolized formulation from a pressurized canister wherein the formulation consists essentially of a free base form of a narcotic drug, a low boiling point propellant liquified under pressure and gaseous under atmospheric pressure, wherein the free base form of the drug is completely dissolved in the propellant; and inhaling the metered dose of aerosolized formulation into the lungs of the patient thereby obtaining a blood plasma level of narcotic of above 1.5 ng/ml within 30 seconds or less from the inhaling.

2. The method of claim 1, wherein the narcotic drug is a free base form of fentanyl.

3. The method of claim 1, wherein the narcotic drug is a free base form of sufentanyl.

4. The method of claim 1, wherein the narcotic drug is a free base form of remifentanyl.

5. The method of claim 1, wherein the narcotic is present in an amount in the range of from about 0.01% to about 1% by weight based on the total volume of the formulation.

* * * * *